(12) United States Patent
Canfield et al.

(10) Patent No.: US 7,543,987 B2
(45) Date of Patent: Jun. 9, 2009

(54) MODULAR COOLING UNIT FOR X-RAY DEVICE

(75) Inventors: Brad Canfield, Orem, UT (US); Ray Daly, Holladay, UT (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 11/025,199

(22) Filed: Dec. 29, 2004

(65) Prior Publication Data

US 2006/0140345 A1 Jun. 29, 2006

(51) Int. Cl.
*H01J 35/10* (2006.01)

(52) U.S. Cl. ......................... 378/200; 378/141; 378/199

(58) Field of Classification Search ................. 378/141, 378/142, 199, 200; 165/78, 122, 80.4
See application file for complete search history.

(56) References Cited

U.S. PATENT DOCUMENTS

| | | | |
|---|---|---|---|
| 4,115,697 A | 9/1978 | Hounsfield et al. | |
| 4,651,338 A | 3/1987 | Hahn et al. | |
| 4,841,557 A | 6/1989 | Haberrecker et al. | |
| 5,482,113 A * | 1/1996 | Agonafer et al. | 165/137 |
| 5,610,968 A * | 3/1997 | Deucher et al. | 378/199 |
| 5,956,383 A * | 9/1999 | Kendall | 378/199 |
| 6,352,103 B1 * | 3/2002 | Chu et al. | 165/80.3 |
| 6,866,577 B2 * | 3/2005 | Gough et al. | 454/184 |
| 6,963,632 B2 * | 11/2005 | Kendall | 378/141 |
| 6,997,609 B2 * | 2/2006 | McCarthy, Jr. | 378/200 |
| 7,056,017 B2 * | 6/2006 | Daniel et al. | 378/200 |
| 7,072,445 B2 * | 7/2006 | Kendall | 378/141 |
| 7,416,333 B2 * | 8/2008 | Zhang et al. | 378/199 |

* cited by examiner

*Primary Examiner*—Allen C. Ho
(74) *Attorney, Agent, or Firm*—Workman Nydegger (57) ABSTRACT

An x-ray imaging system is disclosed, where one example of such a system includes a frame or other structure to which a modular cooling unit of the x-ray imaging system is attached. The modular cooling unit includes a radiator, configured for fluid communication with an x-ray tube housing, as well as one or more fans configured to cause a flow of air to pass through the radiator. In this example, the x-ray imaging system further includes a detector array arranged to receive x-rays generated by an x-ray tube insert disposed within the x-ray tube housing. In operation, the air flow caused by the fans of the modular cooling unit removes heat from coolant flowing out of the x-ray tube housing and through the radiator.

22 Claims, 7 Drawing Sheets

MODULAR COOLING UNIT FOR X-RAY DEVICE

BACKGROUND OF THE INVENTION

1. Field of the Invention

The present invention relates generally to x-ray systems, devices, and related components. More particularly, exemplary embodiments of the invention concern cooling systems and components for x-ray imaging systems.

2. Related Technology

The ability to consistently develop high quality radiographic images is an important element in the usefulness and effectiveness of x-ray devices as diagnostic tools. However, various factors relating to the construction and/or operation of the x-ray device often serve to materially compromise the quality of radiographic images generated by the device. Such factors include, among others, and various thermally induced effects such as the occurrence of physical changes in the x-ray device components as a result of high operating temperatures and/or thermal gradients.

The physical changes that occur in the x-ray device components as a result of the relatively high operating temperatures typically experienced by the x-ray device are of particular concern. Not only do the high operating temperatures impose significant mechanical stress and strain on the x-ray device components, but the heat transfer effected as a result of those operating temperatures can cause the components to deform, either plastically or elastically.

While plastic deformation of an x-ray device component is a concern because it may be symptomatic of an impending failure of the component, elastic deformation of the x-ray device components under high heat conditions is problematic as well. For example, as the various components and mechanical joints are subjected to repeated elastic deformation under the influence of thermal cycles, the connections between the components can loosen and the components may become misaligned or separated. In addition, the elastic deformation of x-ray device components has significant implications as well with respect to the performance of the x-ray device.

Accordingly, various cooling systems, components and devices have been considered in an effort to effectively address the problems implicated by the high operating temperatures and thermal cycles typically experienced in x-ray devices and imaging system environments. As discussed below however, typical cooling systems and devices have proven to be problematic.

One purported solution to the thermal problems presented by x-ray devices and imaging systems involves the use of a unified cooling system cabinet that is in fluid communication with the housing of an x-ray tube. Typically, the cooling system cabinet is an integral element of the x-ray tube. That is, the x-ray tube and cooling system cabinet are manufactured and sold together as an integral, replaceable, unit. Often, such integral units are constructed so that the cooling system cabinet serves as a mounting interface that enables mounting of the integral unit to an associated x-ray imaging system. In other cases, major elements of the cooling system, such as heat exchangers and fans, are attached directly to the housing of the x-ray tube, so that no cooling system cabinet is required. While cooling systems such as those just described may be able to provide useful thermal effects in some situations, significant problems with this type of integrated approach nonetheless remain.

For example, because the cooling system cabinet and the x-ray tube are manufactured as an integral unit, any defect in any portion of the integral unit, even where the defect may be as minor as a cosmetic scratch on the cooling system cabinet, or a premature failure of a cooling system component, can serve as adequate grounds for rejection of the entire unit, either at the incoming inspection by the manufacturer quality assurance department, or by the end customer. In particular, even if the identified defect(s) could be easily remedied in the field, quality assurance standards typically require that the entire unit be rejected by the manufacturer. In the event that a defect, however minor, is first discovered by the customer, warranty limitations would likewise compel the customer to return the unit to the manufacturer, since most customers are disinclined to take any action that could void a warranty on expensive capital equipment such as x-ray systems and equipment.

In either case, the manufacturer is typically compelled to scrap the entire unit. Clearly, this type of practice results in significant, and typically non-recoverable, expense on the part of the manufacturer.

The same general considerations extend to the unit once it is placed in service. In particular, even if a minor component of the tube or the cooling system should fail, such a failure typically necessitates replacement of the entire integrated tube and cooling system unit. In addition to the significant expense involved in the purchase of a replacement unit, service personnel time and shipping costs must also be considered. As well, the replacement of the entire unit in such situations results in the waste of the other remaining components of the unit, notwithstanding that such components may still be fully functional and operational. Further, replacement of the entire unit also increases system down time.

Yet another concern with integral units that include both a cooling system cabinet and x-ray tube relates to the relative differences in the respective service lives of components of the integral unit. By way of example, it is sometimes the case that a cooling fan located in the cooling system cabinet has a relatively shorter service life than other components of the integral unit. As a result, the life of the unit as a whole is largely dictated by the expected life of the fan, or the life of whichever other component(s) are most likely to fail first.

In view of the foregoing, and other, problems in the art, it would be useful to provide an x-ray imaging system that includes a modular cooling unit. Exemplary embodiments of the modular cooling unit should be configured and arranged so that constituent components of the modular cooling system can be readily removed and replaced without necessitating the replacement of the x-ray tube insert and housing, or other system components. In addition, such embodiments of the modular cooling unit should be constructed and implemented so as to allow for relative differences in the service lives of elements of the x-ray imaging system.

BRIEF SUMMARY OF AN EXEMPLARY EMBODIMENT OF THE INVENTION

In general, embodiments of the invention are concerned with cooling systems and components for x-ray imaging systems. In one exemplary embodiment, an x-ray imaging system is provided that includes a modular cooling unit. In this implementation, the modular cooling unit is configured so that an x-ray tube housing, containing an x-ray tube insert, can be removably mounted to, and connected with, the modular cooling unit of the x-ray imaging system.

The exemplary modular cooling unit includes a heat exchanger generally configured and arranged to remove heat from the x-ray tube housing. The heat exchanger includes one or more fans, a pump, and a radiator. A fan mount of the modular cooling unit receives the radiator and positions the fans such that the fans are able to direct a flow of air through the radiator. Additionally, the fan mount enables attachment of the modular cooling unit to a frame, or other structure, of the x-ray imaging system. Finally, a sealing element, such as a gasket for example, is provided that substantially prevents air from the fans from escaping between the fan mount and radiator.

Because the x-ray imaging system is configured to allow temporary removal of the x-ray tube from the modular cooling unit, the components of the modular cooling unit can be readily removed and replaced in the field without necessitating the replacement of the x-ray tube as well. In similar fashion, the ready separability of the modular cooling unit and the x-ray tube enables removal and replacement of the x-ray tube without necessitating replacement of elements of the modular cooling unit.

BRIEF DESCRIPTION OF THE DRAWINGS

In order that the manner in which the above-recited and other aspects of the invention are obtained, a more particular description of the invention briefly described above will be rendered by reference to specific embodiments thereof which are illustrated in the appended drawings. Understanding that these drawings depict only exemplary embodiments of the invention and are not therefore to be considered limiting of its scope, the invention will be described and explained with additional specificity and detail through the use of the accompanying drawings in which.

DETAILED DESCRIPTION OF EXEMPLARY EMBODIMENTS OF THE INVENTION

Reference will now be made to the drawings to describe various aspects of exemplary embodiments of the invention. It should be understood that the drawings are diagrammatic and schematic representations of such exemplary embodiments and, accordingly, are not limiting of the scope of the present invention, nor are the drawings necessarily drawn to scale.

Generally, embodiments of the invention are concerned with x-ray imaging systems and associated cooling systems and components. As discussed more particularly below, exemplary implementations provide for an x-ray imaging system that includes a modular cooling unit to which an x-ray tube is mounted. The modular cooling unit is configured to allow removal of the x-ray tube, either to facilitate replacement of the x-ray tube unit, and/or to permit removal and replacement of elements of the modular cooling unit. In this way, the overall piece count of the system is reduced, and the number of elements removed and replaced is kept to a minimum.

I. An Exemplary X-Ray System

Details will now be provided concerning an exemplary implementation of an x-ray system, denoted generally at 100. While various aspects of exemplary embodiments of the invention are discussed in the context of x-ray systems, devices and related components, the scope of the invention is not limited to any particular type of, or application for, such x-ray systems, devices and related components. For example, aspects of the disclosure are applicable to systems where the radiation source is stationary, relative to the subject, as well as to systems where the radiation source moves relative to the subjects, such as computed tomography ("CT") systems for example. Similarly, some embodiments of the invention are employed in treatment systems, while other embodiments of the invention find application in diagnostic systems. Accordingly, the scope of the invention should not be construed to be limited solely to the exemplary embodiments and applications disclosed herein.

Figure 1:
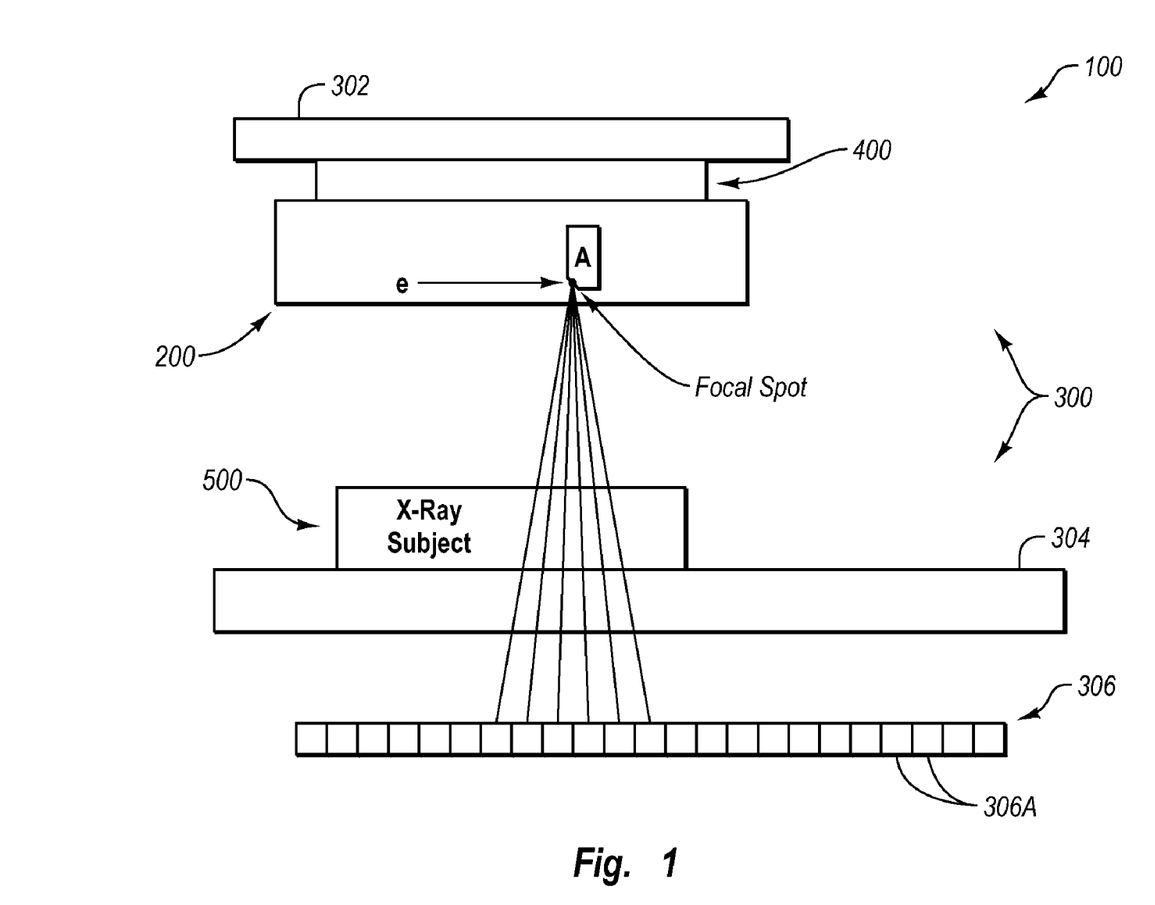
FIG. 1 is a simplified block diagram indicating the relative arrangement of various components of an exemplary x-ray system that includes an x-ray tube and a modular cooling unit of an x-ray imaging system of the x-ray system.

With particular attention now to FIG. 1, the exemplary x-ray system 100 includes an x-ray tube 200 within which is disposed an x-ray tube insert (see FIGS. 3A and 3B) including an anode assembly, denoted generally at "A." The x-ray tube 200 is removably attached to an x-ray imaging system 300 and configured and arranged to interface with a modular cooling unit 400 of the x-ray imaging system 300. As disclosed in further detail elsewhere herein however, the arrangement of the x-ray tube 200 and modular cooling unit 400 can be implemented in a variety of different ways in order to suit operating requirements and/or other circumstances. Thus, the foregoing exemplary arrangement of the modular cooling unit 400 and x-ray tube 200 is exemplary only and are not intended to limit the scope of the invention in any way.

In any case, exemplary arrangements of the modular cooling unit 400 and x-ray tube 200 are such that the components of the modular cooling unit 400 can be readily removed and replaced in the field without necessitating the replacement of the x-ray tube 200 as well. Similarly, the configuration and arrangement of the modular cooling unit 400 and the x-ray tube 200 enables removal and replacement of the x-ray tube 200 without necessitating replacement of some or all of the elements of the modular cooling unit 400.

With continuing reference to FIG. 1, the exemplary x-ray imaging system 300 includes a frame 302 to which the modular cooling unit 400 is attached. The frame 302 refers generally to the structure of the x-ray imaging system 300 and, as such, may include or embrace, for example, a movable gantry and/or other structural element(s) of the x-ray imaging system 300. As referred to in this way, the frame 302 is not intended to limit the scope of the invention to any particular structural element(s).

Where the frame 302 comprises a gantry or portion thereof, the gantry is configured so that the position of the x-ray tube 200, specifically the anode assembly "A," relative to a subject 500 can be adjusted if desired. As indicated, the subject 500 resides on a table 304 that is positioned so that x-rays originating from the focal spot of the anode assembly "A" will pass through the subject 500 and be detected by a detector array 306, of the x-ray imaging system. In this implementation, the detector array 306 includes a plurality of detectors 306A that gather information which is then compiled to produce a complete x-ray image.

II. Modular Cooling Unit

Figure 2A:
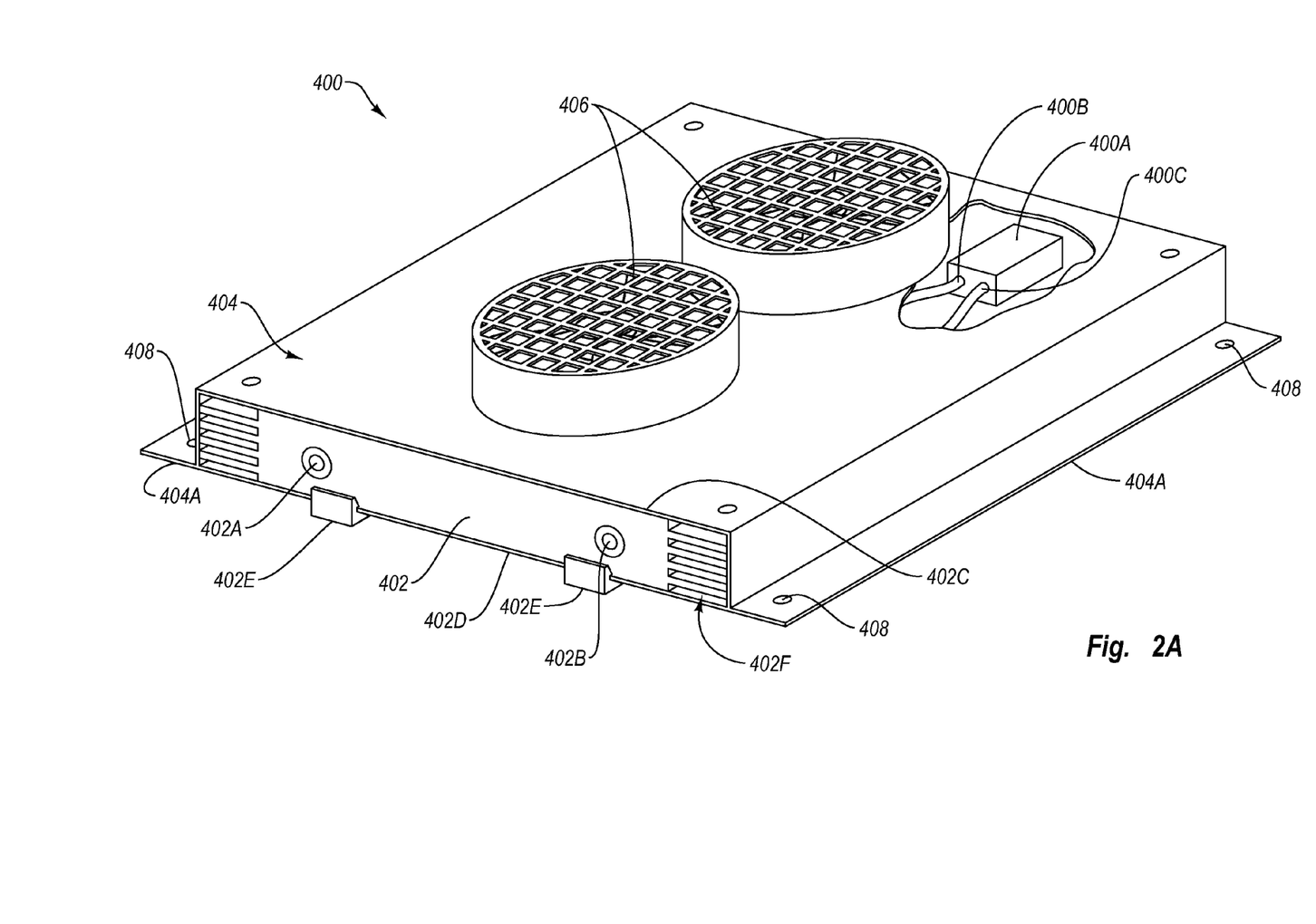
FIG. 2A is a perspective view of an exemplary implementation of a modular cooling unit.

Directing attention now to FIG. 2A, details are provided concerning an exemplary embodiment of a modular cooling unit, denoted generally at 400. As noted earlier, a heat exchanger of the modular cooling unit 400 includes one or more fans, a pump, and a radiator. Accordingly, the illustrated embodiment includes a radiator 402 having coolant inlet and outlet connections 402A and 402B, respectively, and a top 402C and bottom 402D. In alternative embodiments however, the coolant connections 402A and 402B may be reversed.

The radiator 402 is exemplarily implemented as a single pass fluid-to-fluid heat exchanger, such a liquid-gas heat exchanger, but may be implemented in any other form that would provide the requisite heat transfer functionality. Thus, as used herein, the term "radiator" embraces any system, device or combination thereof that implements or facilitates heat transfer functionality. For example, liquid-liquid single pass heat exchangers or multiple pass liquid-liquid or liquid-gas heat exchangers may be alternatively employed. As discussed in further detail below, exemplary gases used in connection with the radiator 402 include air. More generally, embodiments of the radiator may be designed and implemented as necessary to facilitate achievement of a desired heat transfer effect.

Typically, embodiments of the radiator 402 comprise metallic material(s) that are compatible with the demands of x-ray operations, and that are compatible with the coolant(s) desired to be employed in the cooling of the x-ray device. Examples of such metallic materials include, but are not limited to, copper and copper alloys. The scope of the invention should not, however, be limited to the aforementioned exemplary materials.

As to the coolants employed in connection with embodiments of the radiator 402, it should be noted that as used herein, "fluid" refers to liquids, gases, and combinations thereof. For example, some implementations of the radiator 402 may use refrigerants which, during the various stages of operation of an associated x-ray system, may substantially comprise a liquid phase, a gas phase, and/or a combination of liquid and gas phases. At least some implementations of the radiator 402 are suited for use with coolants that substantially comprise ethylene glycol, while other embodiments of the radiator 402 are used in connection with various dielectric oil coolants.

In at least some embodiments of the invention, the radiator 402 is configured to be slidingly received within the fan mount 404, implemented in the illustrated embodiment as a fan bracket, so that the radiator 402 can be readily removed for service or replacement. To this end, exemplary embodiments of the radiator 402 include suitable brackets, clips or other retention devices 402E that enable the radiator 402 to be removably retained within a fan mount 404, discussed below. Any structure having functionality comparable to that provided by such retention devices 402E may alternatively be employed however.

As well, at least some embodiments of the radiator 402 include one or more extended surfaces 402F. Such extended surfaces 402F, which may take the form of fins for example, serve to increase the overall heat transfer area of the radiator 402 and, accordingly, contribute to a relative increase in heat transfer rates that can be achieved with the radiator 402. Parameters such as the number, size, geometry, spacing, positioning and orientation of the extended surfaces 402F may be adjusted as required. The extended surfaces 402F exemplarily comprise copper, or a copper alloy, but may comprise any other suitable material as well. Because exemplary embodiments provide for a radiator 402 that can be readily removed from the fan mount 404, the extended surfaces 402F, and other portions of the radiator 402, can be readily cleaned when necessary. This aspect of exemplary embodiments of the invention is particularly useful in environments, such as hospitals for example, where lint and other materials can be drawn into the radiator and thus impair the effectiveness of the radiator.

Figure 3A:
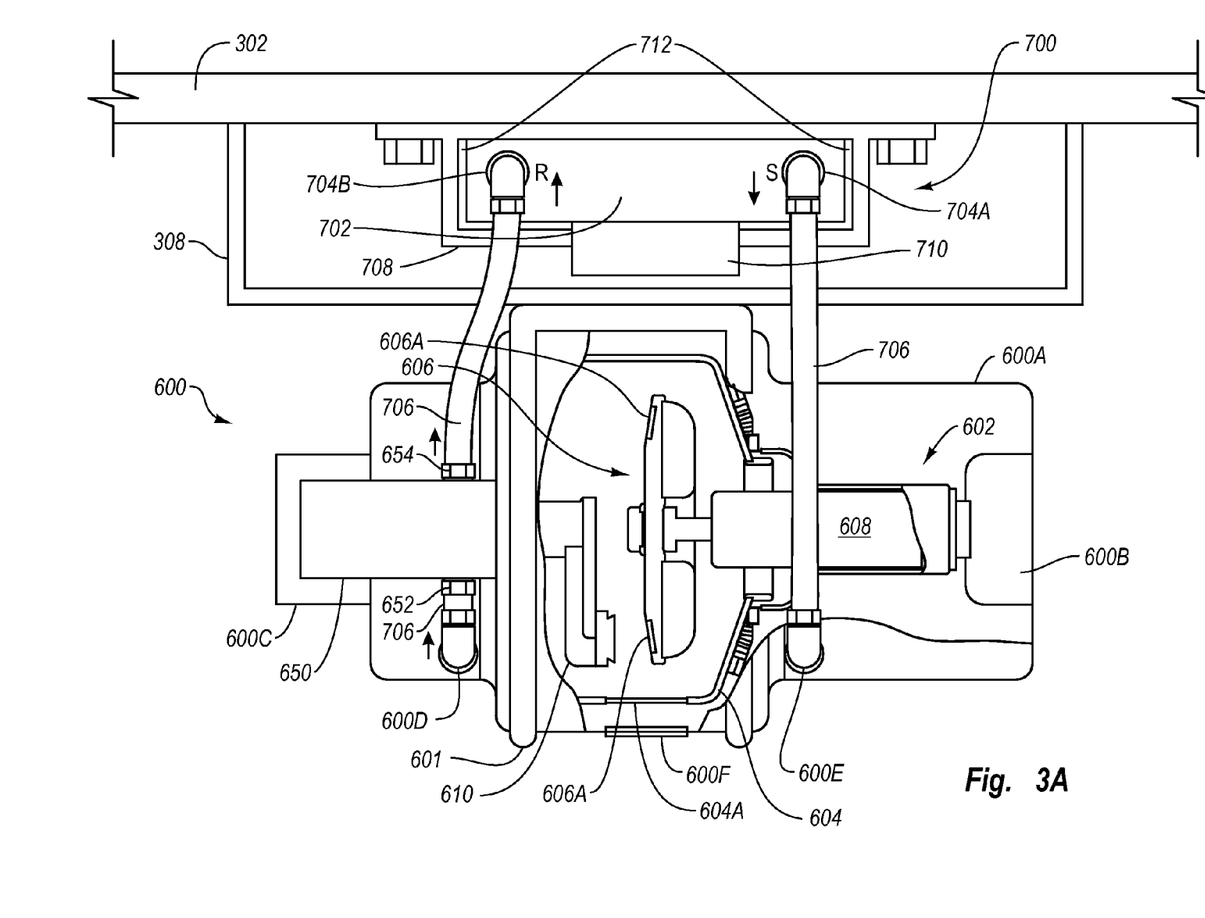
FIG. 3A is a side view showing an exemplary arrangement of a modular cooling unit and x-ray device where a coolant pump is located on the x-ray device.
Figure 3B:
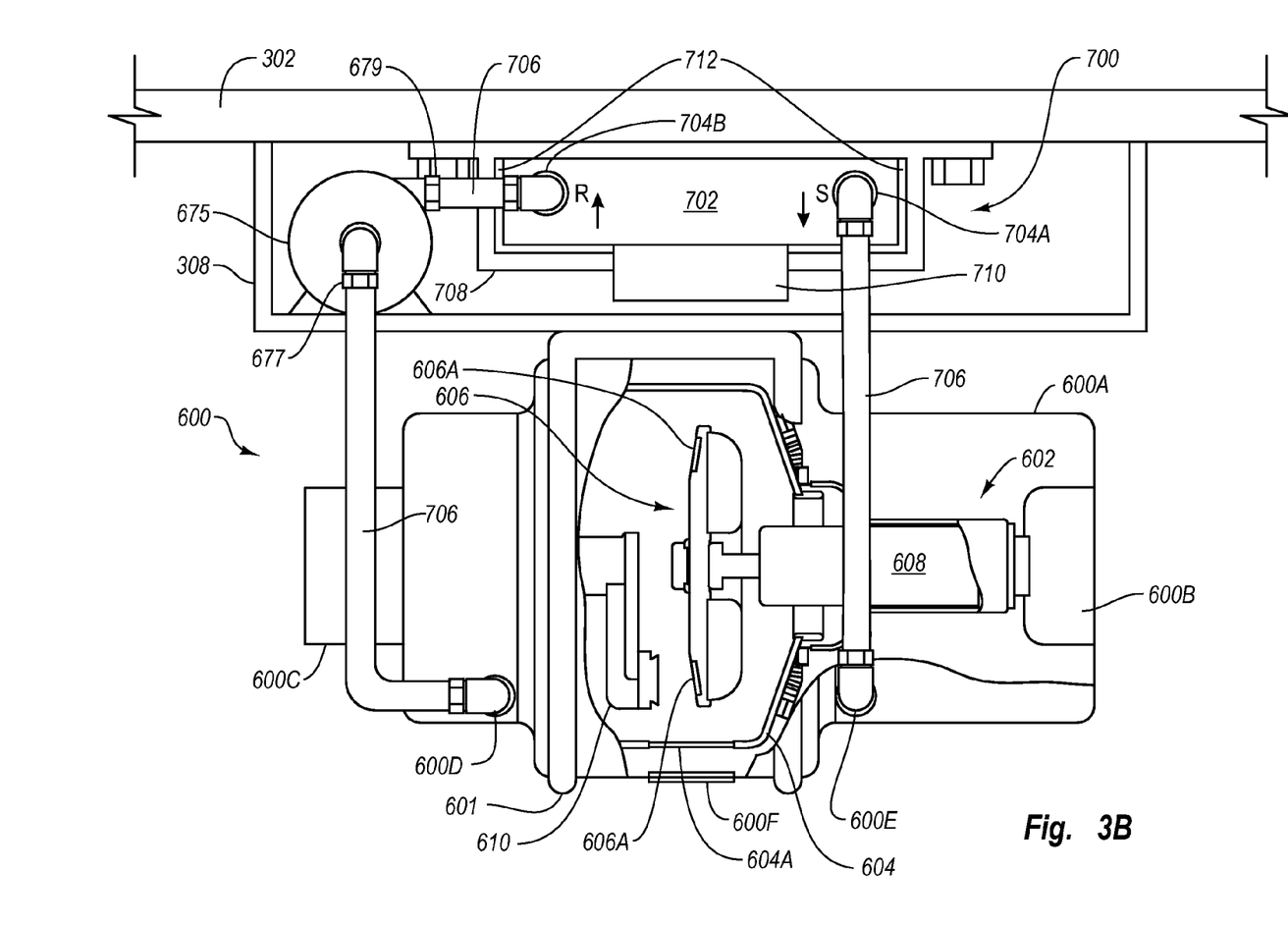
FIG. 3B is a side view showing another arrangement of a modular cooling unit and x-ray device where a coolant pump is separate from both the x-ray device and the modular cooling unit.

In addition to the radiator 402, the exemplary modular cooling unit 400 includes a coolant pump 400A having coolant connections 400B and 400C. Generally, the coolant pump 400A pumps coolant from the radiator 402 and through an x-ray tube housing (not shown). In some alternative implementations of the modular cooling unit, the coolant pump is a separate component and not an element of the modular cooling unit. Two examples of such arrangements are illustrated in FIGS. 3A and 3B, respectively, and discussed in detail below.

With continuing attention to FIG. 2A, the exemplary modular cooling unit 400 further includes a fan mount 404 which, among other things, serves to position one or more fans 406 in desired locations relative to the radiator 402, and also provides an avenue for mounting the modular cooling unit 400 to structure of the x-ray imaging system 300. The fan mount 404 is implemented in FIG. 2A as a fan bracket while, in FIG. 2B, the fan mount takes the form of an adapter plate, discussed below.

Embodiments of the fan mount 404 comprise one or more pieces of sheet metal, such as steel or aluminum for example, that define an enclosure which at least partially houses the radiator 402, and coolant pump if supplied. Where multiple pieces of material are employed to construct the fan mount 404, those pieces can be joined together in any suitable fashion, such as with fasteners, or by welding, soldering, brazing or other suitable processes. Additionally, structural pieces, such as angles and flat bar for example, may be substituted for sheet metal. Non-metallic materials may also be employed in the construction of the fan mount 404. As the foregoing thus makes clear, the scope of the invention is not limited to any particular configuration or construction materials for embodiments of the fan mount 404.

In the illustrated embodiment, both the top 402C and bottom 402D of the radiator 402 are substantially enclosed by the fan mount 404. In other embodiments however, the fan mount 404 is configured as a fan bracket substantially in the shape of a "U" having an open portion positioned such that the bottom 402D of the radiator 402 is not enclosed, as in the case of the alternative embodiment illustrated in FIG. 2B. More generally, and as disclosed herein, the fan mount 404 can be configured in any other way consistent with the desired functionality.

The illustrated exemplary fan mount 404 further defines one or more flanges 404A configured to receive fasteners 408 so that the fan mount 404, radiator 402 and fans 406 of the modular cooling unit 400 can be removably attached to structure of the x-ray imaging system 300, such as the frame 302 for example. In one alternative implementation, one or more of the flanges 404A are replaced with suitable mounting brackets, but any other structure(s) of comparable functionality may likewise be employed.

As noted earlier, the fan mount 404 not only facilitates positioning and retention of the radiator 402, as well as the mounting of the modular cooling unit 400, but the fan mount 404 also serves to position one or more fans 406 in desired locations and orientation relative to the radiator 402 so that at least some of the heat can be removed from coolant flowing through the radiator 402. With continuing attention now to FIG. 2A, further details are provided concerning the use of one or more fans 406 in connection with an exemplary embodiment of the modular cooling unit 400.

In the embodiment illustrated in FIG. 2A, the fan mount 404 serves to position a pair of fans 406 proximate the radiator 402 so that, as discussed in further detail below in connection with FIGS. 3 and 4, the fans 406 cause a flow of air to pass through the radiator 402, thereby removing some of the heat in the coolant flowing from the x-ray tube housing and into the radiator 402. In some embodiments, the fans 406 are configured and arranged so that air is pulled into the fan mount 404 and through the radiator 402 by the fans 406. In an alternative arrangement, the fans 406 are configured and arranged to push a flow of air through the radiator 402.

The fan(s) 406 employed in the modular cooling unit 400 typically comprise electrically powered fans and may be any type of fan effective in facilitating a desired heat transfer effect. Various types, sizes, and numbers of fans may be employed. Moreover, the positioning, speed, and air movement characteristics of the fans may be selected as desired. Additionally, where multiple fans 406 are employed, the modular cooling unit 400 is, in some embodiments, constructed with circuitry which enables cycling of the fans between the "on" and "off" positions at various time intervals. In some exemplary implementations, intermediate fan speed settings, such as a half speed setting, are implemented in connection with the circuitry. In yet other implementations, the fan speed setting permits analog adjustment over a range of speeds.

More generally, the modular cooling unit 400 includes the circuitry and wiring (not shown) necessary to provide and regulate power to the fans 406. In some embodiments, the modular cooling unit 400 also includes one or more fault circuits and associated indicators or readouts (not shown) for identifying, and providing status concerning, actual or impending failure of one or more of the fans 406, and/or other conditions of interest to an operator or technician.

It should be noted that notwithstanding the aforementioned exemplary characteristics of fans and fan arrangements, the scope of the invention is not limited to the disclosed exemplary embodiments. Rather, any other fans and/or arrangements of air moving devices can be employed that are effective in facilitating achievement of a desired heat transfer effect.

Finally, the illustrated fan mount 404 includes one or more sealing elements (see 409 in FIG. 2B), such as a gasket for example, that serve to prevent the fan airflow, discussed below, from escaping between the fan mount 404 and the radiator 402. The sealing element is composed of any suitable material(s), examples of which include, but are not limited to, rubber, foam rubber, or any other material(s) compatible with the intended application.

Figure 2B:
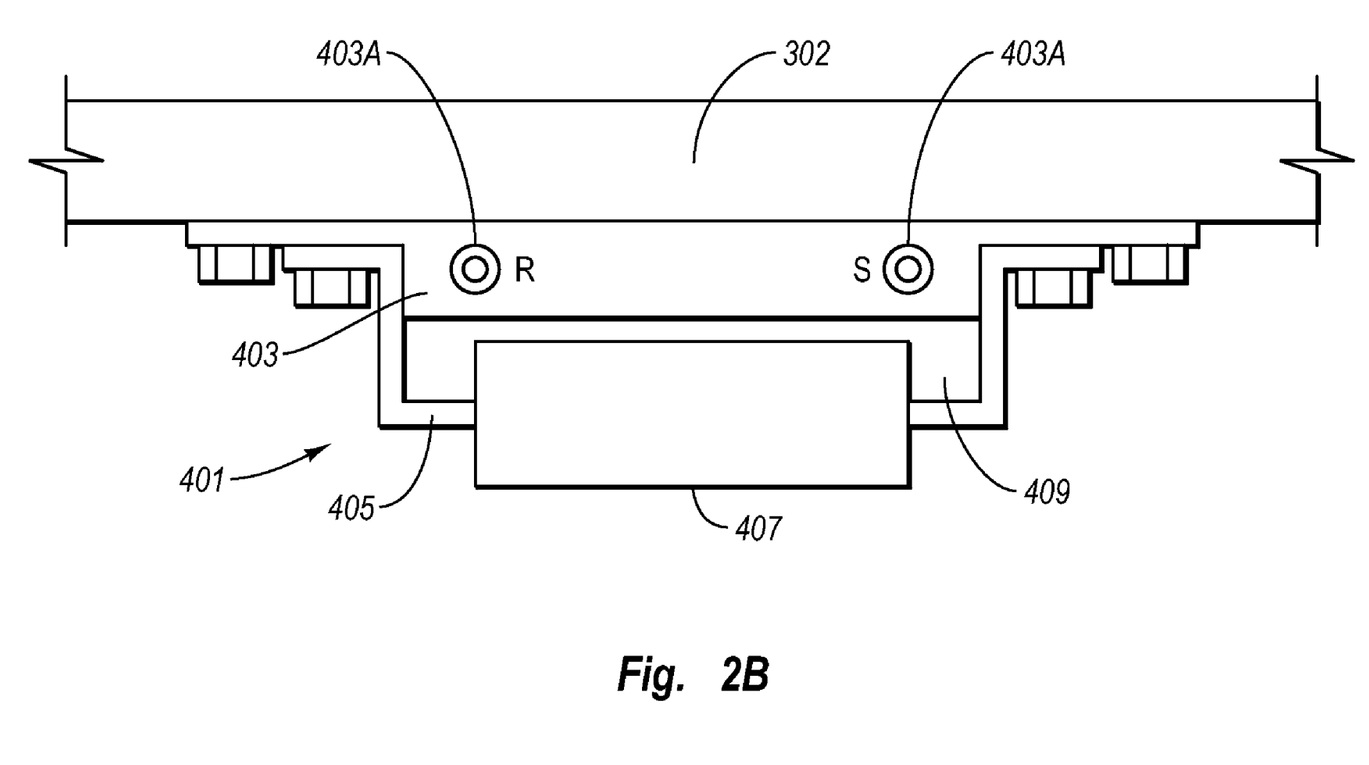
FIG. 2B is a side view of an alternative implementation of a modular cooling unit, as installed on a structural element.

Directing attention now to FIG. 2B, details are provided concerning an alternative embodiment of a modular cooling unit, denoted generally at 401. As the disclosure herein concerning the modular cooling unit 400 is germane in many regards to the modular cooling unit 401, the following discussion will focus primarily on selected distinctions between the two exemplary embodiments.

As indicated in FIG. 2B, the modular cooling unit 401 includes a radiator 403 that is configured to be bolted, or otherwise attached, to the frame 302 or other structure of the x-ray imaging system 300 (see FIG. 1). The radiator 403 includes a pair of coolant connections 403A that permit a flow of coolant to circulate through the radiator 403, as disclosed in further detail elsewhere herein. As discussed below in connection with FIGS. 3 and 4, the radiator 403 is configured for fluid communication with a housing of an x-ray device.

Further, the modular cooling unit 401 includes an adapter plate 405 that is also configured to be bolted or otherwise attached to the frame 302 or other structure. In the illustrated implementation, the adapter plate 405 also bolts to the radiator 403 so that the adapter plate 405 serves to further secure the radiator 403 in position, while also being separately removable. The adapter plate 405 exemplarily comprises metallic materials, examples of which include steel and aluminum.

Among other things, the adapter plate 405 serves to position one or more fans 407 so that the fans 407 are able to cause a flow of air to pass through the radiator 403. In order to further facilitate heat transfer, the modular cooling unit 401 includes a sealing element 409, such as a gasket for example, that substantially prevents air from escaping between the radiator 403 and the adapter plate 405.

As a result of the configuration and arrangement of the elements of the modular cooling unit 401, the fan(s) 407 and/or the radiator 403 can be readily removed and/or replaced without necessitating the removal of the associated x-ray tube (see, e.g., FIGS. 3A and 3B). Similarly, the x-ray tube can be removed and replaced without necessitating the removal of the fan(s) 407 or radiator 403. Thus, another aspect of the construction and arrangement of the modular cooling units disclosed herein, (exemplified in FIGS. 2A and 2B, is that differences in the service life of the various modular cooling unit components and the x-ray tube can be readily accommodated without incurring the undue costs and effort that would likely otherwise result.

In one particular implementation, the pump resides on the x-ray tube and is permanently connected to the radiator, so that only the fans remain on the gantry, or other structure, when the modular cooling unit is removed. In another exemplary implementation however, the pump is connected to the radiator using quick disconnect connections so that the two components can be readily disconnected and reconnected. More generally however, any other components of the modular cooling unit may be similarly configured so as to ensure compatibility with the requirements of a particular installation or operating environment.

III. Arrangement of an X-Ray Tube and Modular Cooling Unit

With attention now to FIG. 3A, further details are provided concerning the structure and arrangement of an x-ray tube, exemplarily implemented as a rotating anode type x-ray tube and denoted generally at 600, and modular cooling unit, denoted at 700 and generally configured as shown in FIG. 2A. Unlike the exemplary modular cooling unit disclosed in FIG. 2A however, the modular cooling unit 700 does not include a coolant pump. Rather, the coolant pump is, as discussed below, attached to the x-ray tube 600. Other than rotating anode type x-ray tubes may be employed as well however. It should likewise be noted that the exemplary modular cooling unit disclosed in FIG. 2B may alternatively be employed and arranged in a fashion similar to that indicated in FIG. 3A with regard to x-ray tube 600.

The x-ray tube 600 is attached, removably in some implementations, to a mounting structure 308, of the x-ray imaging system 300 (FIG. 1), by way of a pair of trunnions 601, though any other structure comparable to trunnions 601 may alternatively be employed. In this implementation, the mounting structure 308 comprises a portion of the frame 302 of the x-ray imaging system 300. In general, the exemplary mounting structure 308 is configured so as to provide a space for the modular cooling unit 700, with the result that the modular cooling unit 700 is positioned between the x-ray tube 600 and the frame 302.

The x-ray tube 600 includes a housing 600A that includes an insert support 600B which provides support to an x-ray tube insert, discussed below. The x-ray tube 600 further includes a pair of high voltage connections, one of which is indicated at 600C, as well as a pair of coolant connections 600D and 600E.

Disposed within the housing 600A is an x-ray tube insert 602 with a vacuum enclosure 604 that defines a window 604A through which x-rays generated by the x-ray tube insert 602 are directed. The window 604A comprises beryllium or another suitable material, and is generally aligned with a corresponding window 600F of the x-ray tube 600. A rotating anode 606 is disposed within the vacuum enclosure 604 and is supported by a bearing assembly 608 that is configured to attach at least indirectly to the insert support 600B. Finally, a cathode 610, or other electron emitter, is positioned to direct a stream of electrons at a target track 606A of the anode 606. The target track 606A is composed of tungsten or another material(s) suitable for use in the generation of x-rays. In general, the cathode 610 and target track 606A are situated so that a focal spot, defined as the point of impact of the emitted electrons proximate the surface of the target track 606A, remains in a desired position relative to a detector or detector array, such as detector array 306 (see FIG. 1).

In operation, a high voltage potential established between the cathode 610 and the anode 606, by way of the high voltage connections 600C, causes electrons emitted from the cathode 610 to accelerate rapidly towards the target track 606A of the anode 606, striking the target track 606A and causing x-rays to be emitted through the windows 604A and 600F. As discussed in further detail below, at least some of the heat generated as a result of the operation of the x-ray tube insert 602 is removed by way of coolant flowing through the coolant connections 600D and 600E.

With continuing attention to FIG. 3A, details are provided concerning the structure and arrangement of the exemplary modular cooling unit 700 that is configured and arranged to aid in the removal of heat from the x-ray tube 600. As noted earlier, the modular cooling unit 700 is positioned, in this exemplary arrangement, beneath the mounting structure 308 to which the x-ray tube 200 is attached.

The illustrated modular cooling unit 700 includes a radiator 702 with a pair of coolant connections, specifically a supply ("S") connection 704A, by way of which coolant is supplied to the x-ray tube 600, and a return ("R") connection 704B, by way of which heated coolant is received from the x-ray tube 600. The supply and return connections 704A and 704B include suitable threads and/or fittings that permit removable attachment of a corresponding pair of coolant hoses 706. Additionally, or alternatively, each end of the coolant hoses 706 may include various fittings as well. The coolant hoses 706 may be constructed of any material(s) suitable for use in x-ray device operating environments.

Moreover, parameters such as the length and diameter of the coolant hoses 706 may be selected as necessary to suit the requirements of a particular application. In any case, the coolant hoses 706 serve to connect the supply and return connections 704A and 704B of the radiator 702 with the corresponding coolant connections 600E and 600D, respectively, of the x-ray tube housing 600A so that coolant can be circulated from the x-ray tube housing 600A through the radiator 702 and back to the x-ray tube housing 600A.

More particularly, a coolant pump 650 is provided in this exemplary embodiment that is attached to the x-ray tube 600. The coolant pump 650 includes a suction connection 652 by way of which heated coolant is drawn from the x-ray tube housing 600A through coolant hose 706 and into the coolant pump 650. The coolant pump 650 further includes a discharge connection 654 to which coolant hose 706 is attached and by way of which coolant from the x-ray tube housing 600A is discharged from the coolant pump 650 and pumped through the modular cooling unit 700. The coolant hoses 706 include appropriate hose fittings or other devices for attachment to the suction connection 652 and discharge connection 654 of the coolant pump 650. In at least some embodiments, the coolant hoses 706 are configured to be removably attached to the suction connection 652 and discharge connection 654 of the coolant pump 650.

Note that while the coolant pump 650 is located in the coolant return line to the radiator 702 in this exemplary implementation, other arrangements may alternatively be employed. For example, in some alternative arrangements, the coolant pump 650 is a located in the coolant supply line to the x-ray tube housing 600A.

At least some implementations of the invention further include a variety of additional circuits and components to facilitate control of the cooling of the x-ray tube 600. Such other circuits and components include, for example, flow regulators and flow control valves to control and monitor coolant flow rates through the housing 600A, high temperature alarms and indicators to indicate excessively high coolant temperatures stemming from coolant system faults, temperature and pressure indicators to provide feedback concerning aspects of the coolant flow through the radiator 702 and/or housing 600A, and high temperature cutout switches and circuitry to curtail or prevent operation of the x-ray tube 600 in the event that the coolant temperature exceeds a predetermined limit and/or if coolant flow drops below an acceptable rate.

With continuing attention to the arrangement disclosed in FIG. 3A, a fan bracket 708 of the modular cooling unit 700 substantially encloses and retains the radiator 702 which, in one alternative arrangement, is supplied to an end user with the x-ray tube 600. In the illustrated embodiment, the radiator 702 is substantially enclosed within, and slidingly received by, the fan bracket 708. Depending upon the implementation, the radiator 702 may alternatively be permanently, or removably, attached to the frame 302. Additionally, the fan bracket 708 is attached to the frame 302, thus, the modular cooling unit 700, or the fans 710 at a minimum, is/are implemented as part of the x-ray imaging system 300. In some cases, the fan bracket 708 is removably attached to the frame 302 while, in other implementations, the fan bracket 708 is permanently attached to the frame 302.

In either case however, the fans 710, discussed below, are removably attached to the fan bracket 708. As a result of this configuration and arrangement, the radiator 702 and/or fans 710 can be readily removed and/or replaced, without necessitating replacement of the entire x-ray tube 600. Likewise, because the modular cooling unit 700 and the x-ray tube 600 are discrete, separable components, removal and replacement of the x-ray tube 600 can be effected without necessitating replacement of elements of the modular cooling unit 700.

With continuing attention to FIG. 3A, the fan bracket 708 serves to position one or more fans 710 so that when one or more of the fans 710 are activated, a flow of air from the fans 710 is directed through the radiator 702. In this way, at least some of the heat present in coolant entering the radiator 702 by way of the coolant return connection 704B is removed prior to the return of the coolant to the x-ray tube 600.

In order to further enhance heat transfer effects achieved in connection with the fans 710 and radiator 702, the illustrated modular cooling unit 700 further includes one or more sealing elements 712 which substantially prevent leakage of air from between the fan bracket 708 and radiator 702.

Directing attention now to FIG. 3B, details are provided concerning an alternative arrangement of the x-ray tube 600 and the modular cooling unit 700. As the arrangement disclosed in FIG. 3B is similar in many regards to that disclosed in FIG. 3A, the following discussion of FIG. 3B will primarily be limited to certain differences between the two arrangements.

One of the distinctions between the arrangement of FIG. 3B and that of FIG. 3A concerns the location of the coolant pump, denoted at 675 in FIG. 3B. In particular, the coolant pump 675 is attached to the mounting structure 308. In the illustrated arrangement, the coolant pump 675 is disposed within the mounting structure 308, but the coolant pump 675 may alternatively be attached to an exterior portion of the mounting structure 308. The attachment of the suction connection 677 of the coolant pump 675, by way of coolant hose 706 and appropriate fittings, to the x-ray tube housing 600A is generally similar to the arrangement indicated in FIG. 3A. The same is correspondingly true with respect to the attachment of the discharge connection 679, by way of coolant hose 706 and appropriate fittings, of the coolant pump 675 to the radiator 702.

IV. Operational Considerations

Figure 4:
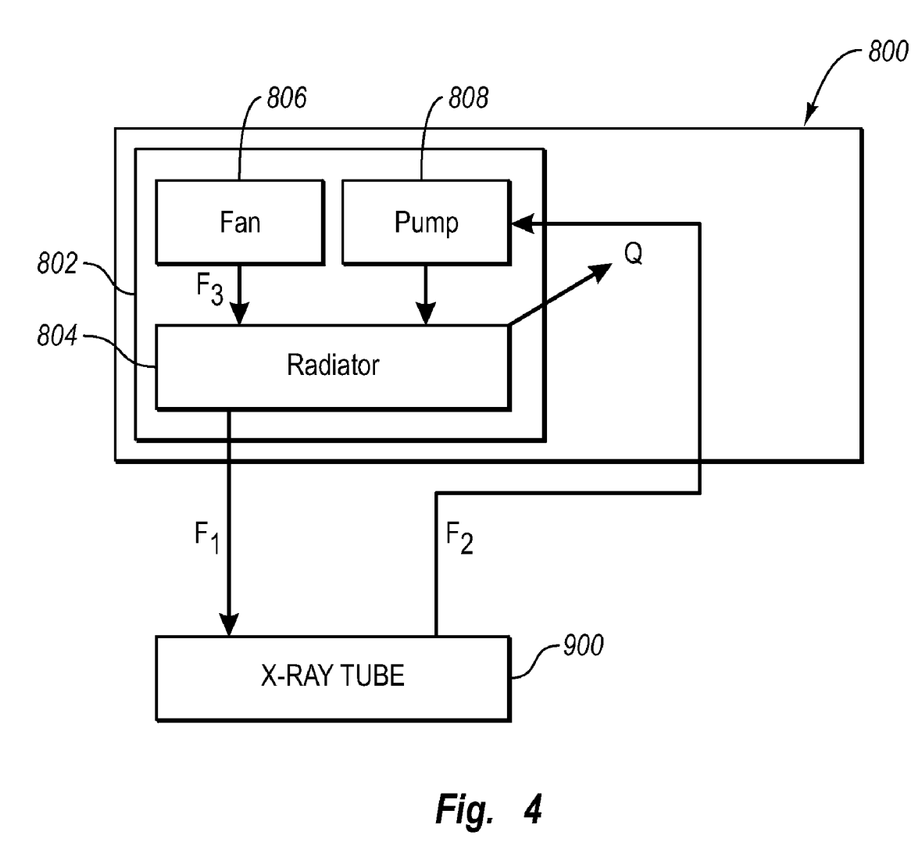
FIG. 4 is a block diagram indicating aspects of heat transfer functionality implemented in connection with exemplary embodiments of the invention.

With attention now to FIG. 4, and with continuing attention to FIG. 3B, details are provided concerning various operational aspects of a system such as is exemplified in FIG. 3B. More particularly, FIG. 4 illustrates an exemplary arrangement of an x-ray imaging system 800, that includes a modular cooling unit 802 having a radiator 804, one or more fans 806 and an x-ray tube 900 within which is disposed an x-ray tube insert (not shown).

A coolant pump 808 is also provided that, in exemplary FIG. 4, is part of the x-ray imaging system 800, but is separate from the x-ray tube 900. As discussed elsewhere herein, the coolant pump may be included as an element of the modular cooling unit (see, e.g., FIG. 2A), or may comprise an element separate from both the modular cooling unit and the x-ray tube housing (see, e.g., FIG. 3B), or may comprise an element of the x-ray tube (see, e.g., FIG. 3A and FIG. 5). Accordingly, the arrangements disclosed in the figures are exemplary only and are not intended to limit the scope of the invention in any way.

In operation, at least some of the heat generated as a result of x-ray tube operations is transferred to coolant pumped by the coolant pump 808 at flow rate $F_1$ from the radiator 804. The heated coolant then exits the housing of the x-ray tube 900 at flow rate $F_2$, which is typically the same as flow rate $F_1$, and returns to the pump 808. At the same time, one or more fans 806 cause air flowing at rate $F_3$ to come into contact with heat transfer surfaces of the radiator 804. As a result of this air flow, which may comprise a flow of air either pulled or pushed through the radiator 804, heat Q is removed from coolant flowing through the radiator 804 at a corresponding rate. As the foregoing suggests, changes to the rate at which heat Q is removed from the flowing coolant and, thus, from the x-ray tube insert, can be effected by varying parameters including, but not limited to, the air flow rate $F_3$, and the coolant flow rates $F_1$ & $F_2$.

Figure 5:
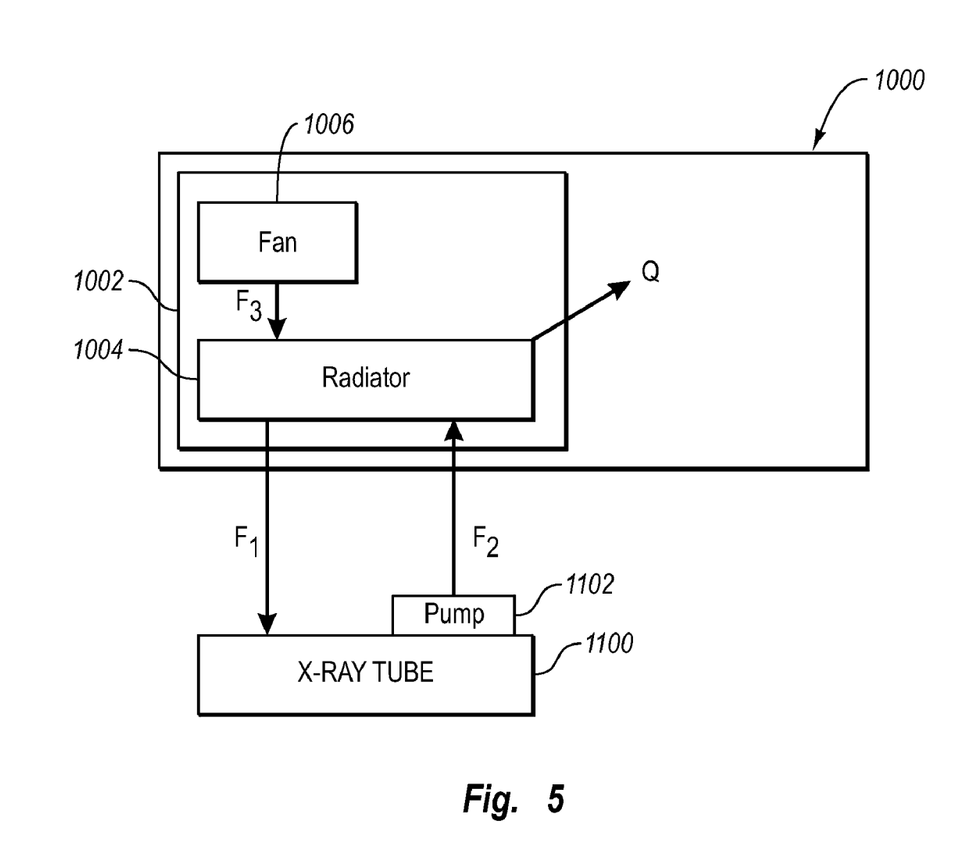
FIG. 5 is a block diagram indicating aspects of heat transfer functionality implemented in connection with an alternative embodiment of the invention.

Directing attention finally to FIG. 5, details are provided concerning an alternative configuration and arrangement of an x-ray imaging system 1000 that includes a modular cooling unit denoted generally at 1002 configured to operate in connection with an x-ray tube 1100. In the illustrated arrangement, the modular cooling unit 1002 includes a radiator 1004 and one or more fans 1006. This arrangement differs from that of FIG. 4 in that the coolant pump, denoted at 1102, comprises an element of the x-ray tube 1100.

Operationally, the arrangement illustrated in FIG. 5 is similar to that of other embodiments disclosed herein. In particular, at least some of the heat generated as a result of x-ray tube 1100 operations is transferred to coolant which enters the x-ray tube 1100 at flow rate $F_1$ from the radiator 1004. The heated coolant is then pumped out of the x-ray tube 1100 by the coolant pump 1102 at flow rate $F_2$, which is typically the same as flow rate $F_1$, and back to the radiator 1004.

At the same time, one or more fans 1006 cause air flowing at rate $F_3$ to come into contact with heat transfer surfaces of the radiator 1004. As a result of this air flow, which may comprise a flow of air either pulled or pushed through the radiator 1004, heat Q is removed from coolant flowing through the radiator 1004 at a corresponding rate. As the foregoing suggests, changes to the rate at which heat Q is removed from the flowing coolant and, thus, from the x-ray tube insert, can be effected by varying parameters including, but not limited to, the air flow rate $F_3$, and the coolant flow rates $F_1$ & $F_2$.

The described embodiments are to be considered in all respects only as exemplary and not restrictive. The scope of the invention is thus indicated by the appended claims rather than by the foregoing description. All changes which come within the meaning and range of equivalency of the claims are to be embraced within their scope.

What is claimed is:

1. An x-ray imaging system, comprising:
   a frame;
   a mounting structure attached to the frame;
   an x-ray tube attached to the mounting structure, the x-ray tube including an x-ray tube housing and an x-ray tube insert disposed in the housing;
   a modular cooling unit at least partially disposed within a space collectively defined by the frame and the mounting structure, the modular cooling unit comprising:
      a radiator configured for fluid communication with the x-ray tube housing;
      a fan mount attached at least indirectly to the frame; and
      a fan attached to the fan mount and arranged to cause a flow of air to flow through the radiator; and
   a detector arranged to receive x-rays generated by the x-ray tube insert,
   wherein the mounting structure includes first and second opposing sides, the frame being attached on the first side of the mounting structure, and the x-ray tube being attached on the second side of the mounting structure.

2. The x-ray imaging system as recited in claim 1, wherein the fan mount comprises one of: an adapter plate; and, a fan bracket.

3. The x-ray imaging system as recited in claim 1, wherein the fan mount is configured to be removably attached to the frame.

4. The x-ray imaging system as recited in claim 1, wherein the radiator is slidingly received within the fan mount.

5. The x-ray imaging system as recited in claim 1, wherein the radiator is removably retained within the fan mount.

6. The x-ray imaging system as recited in claim 1, wherein the radiator is configured to be removably attached to the frame.

7. The x-ray imaging system as recited in claim 1, wherein the radiator is held between the fan mount and the frame.

8. The x-ray imaging system as recited in claim 1, wherein the fan is configured and arranged to pull a flow of air through the fan mount and the radiator.

9. The x-ray imaging system as recited in claim 1, wherein the fan is configured and arranged to push a flow of air into the fan mount and the radiator.

10. The x-ray imaging system as recited in claim 1, wherein the frame comprises a gantry.

11. The x-ray imaging system as recited in claim 1, wherein the modular cooling unit further comprises a sealing element disposed between the radiator and the fan mount.

12. The x-ray imaging system as recited in claim 1, wherein the radiator includes at least one extended surface configured for contact with airflow generated by the fan.

13. The x-ray imaging system as recited in claim 1, wherein elements of the modular cooling unit can be removed and replaced without necessitating replacement of the x-ray tube insert.

14. The x-ray imaging system as recited in claim 1, further comprising a coolant pump in fluid communication with the radiator and the x-ray tube housing.

15. The x-ray imaging system as recited in claim 14, wherein the coolant pump is an element of one of: the modular cooling unit; or, the x-ray tube.

16. An x-ray system, comprising:
   an x-ray imaging system, comprising:
      a frame;
      a modular cooling unit, comprising:
         a radiator;
         a fan mount attached at least indirectly to the frame so as to retain the radiator to the frame, the radiator being slidingly received within the fan mount; and
         a fan attached to the fan mount in a manner such that the radiator is positioned substantially between the fan and the frame and the fan being arranged to cause a flow of air to come into contact with the radiator;
      a detector; and
      an x-ray tube that includes an x-ray tube housing containing an x-ray tube insert and mounted to the frame, the x-ray tube housing being configured for fluid communication with the radiator, and the x-ray tube insert being configured and arranged to generate x-rays for reception by the detector.

17. The x-ray system as recited in claim 16, wherein the fan mount comprises one of: an adapter plate; and, a fan bracket.

18. The x-ray system as recited in claim 16, wherein the fan mount is configured to be removably attached to the frame.

19. The x-ray system as recited in claim 16, wherein the radiator is removably retained within the fan mount.

20. The x-ray system as recited in claim 16, wherein elements of the modular cooling unit can be removed and replaced without necessitating replacement of the x-ray tube insert.

21. The x-ray system as recited in claim 16, wherein the x-ray imaging system further comprises a coolant pump in fluid communication with the radiator and the x-ray tube housing.

22. The x-ray imaging system as recited in claim 21, wherein the coolant pump is an element of one of: the modular cooling unit; or, the x-ray tube.

\* \* \* \* \*

UNITED STATES PATENT AND TRADEMARK OFFICE
CERTIFICATE OF CORRECTION

PATENT NO. : 7,543,987 B2  Page 1 of 1
APPLICATION NO. : 11/025199
DATED : June 9, 2009
INVENTOR(S) : Canfield et al.

It is certified that error appears in the above-identified patent and that said Letters Patent is hereby corrected as shown below:

Column 8
Line 28, change ",(exemplified" to --, exemplified--

Signed and Sealed this

Sixth Day of July, 2010

David J. Kappos
*Director of the United States Patent and Trademark Office*